US006526299B2

(12) United States Patent
Pickard (10) Patent No.: US 6,526,299 B2
(45) Date of Patent: Feb. 25, 2003

(54) SPECTRUM PROCESSING AND PROCESSOR

(75) Inventor: David Pickard, London (GB)

(73) Assignee: University College London, London (GB)

( * ) Notice: Subject to any disclaimer, the term of this patent is extended or adjusted under 35 U.S.C. 154(b) by 0 days.

(21) Appl. No.: 09/791,000

(22) Filed: Feb. 22, 2001

(65) Prior Publication Data

US 2002/0137993 A1 Sep. 26, 2002

(30) Foreign Application Priority Data

Feb. 7, 2001 (GB) .............................................. 0103030

(51) Int. Cl.⁷ ................................................ A61B 5/00
(52) U.S. Cl. ...................... 600/310; 600/322; 600/476
(58) Field of Search ................................ 600/309–310, 600/322–324, 330–331, 336, 473, 476; 356/39–42

(56) References Cited

U.S. PATENT DOCUMENTS

| | | | |
|---|---|---|---|
| 5,303,026 A | | 4/1994 | Strobl et al. ................. 356/318 |
| 5,353,790 A | | 10/1994 | Jacques et al. |
| 5,421,339 A | * | 6/1995 | Ramanujam et al. ....... 600/477 |
| RE35,148 E | * | 1/1996 | Lizzi et al. .................. 348/163 |
| 5,974,337 A | * | 10/1999 | Kaffka et al. ............... 600/316 |
| 6,280,381 B1 | * | 8/2001 | Malin et al. ................. 600/322 |

FOREIGN PATENT DOCUMENTS

| | | | | |
|---|---|---|---|---|
| EP | 0906936 A1 | 4/1999 | ........... | C08L/29/04 |
| WO | WO 97/41777 | 11/1997 | | |
| WO | WO 98/27865 | 7/1998 | | |

OTHER PUBLICATIONS

Mourant, J. et al., "Spectroscopic Diagnosis of Bladder Cancer with Elastic Light Scattering", Lasers in Surgery and Medicine, vol. 17 pp. 350–357 (1995).

Mourant, J. et al., "Elastic Scattering Spectroscopy as a Diagnostic Tool for Differentiating Pathologies in the Gastrointestinal Tract: Preliminary Testing", Journal of Biomedical Optics vol. 1, No. 2., pp. 192–199 (Apr. 1996).

Irving J. Bigio and Judith R. Mourant, "Ultraviolet and visible spectroscopies for tissue diagnostics: fluorescence spectroscopy and leastic–scattering spectroscopy", Phys. Med. Biol., vol. 42, pp. 803–813 (1997).

(List continued on next page.)

Primary Examiner—Eric F. Winakur
Assistant Examiner—Matthew Kremer
(74) Attorney, Agent, or Firm—Darby & Darby (57) ABSTRACT

An elastic scattering spectrum taken from human tissue is taken and preprocessed by dividing the absorption spectrum into a plurality of wavelength ranges and fitting the measured absorption spectrum to the absorption of predetermined absorption components in some fitting ranges and to a smooth function, such as a straight line, in the remainder of the fitting ranges. The absorption components may include, for example, haemoglobin.

25 Claims, 5 Drawing Sheets

OTHER PUBLICATIONS

V Backman et al., "Detection of Preinvasive cancer cells", Nature, vol. 406, pp 35–36 Jul. 6, 2000.

L.T. Perelman et al., "Observation of Periodic Fine Structure in Reflectance from Biological Tissue: A New Technique for Measuring Nuclear Size Distribution", Physical Review Letters, vol. 80, No. 3, pp. 627–630, Jan. 19, 1998.

Zhengfang GE et al., "Identification of Colonic Dysplasia and Neoplasia by Diffuse Reflectance Spectroscopy and Pattern Recognition Techniques", Applied Spectroscopy, vol. 52, No. 6, pp 833–839 (1998).

D Pickard et al., "Diagnosis of Dysplasia in Barrett's Oesophagus with In–Situ Elastic–Scattering Spectroscopy", EBIOS 2000, (SPIE European Biomedical Optics Symposium, Jul. 2000, Amsterdam).

S.G. Brown et al., Material related to "Optical Biopsy for the Diagnosis of Breast Tumors" (including Scientific abstract, Lay Abstract, and a brochure), Era of Hope (US Army Material Command, Jun. 2000, Atlanta, Georgia).

L.B. Lovat et al., "A Novel Optical Biopsy Technique using Elastic Scattering Spectroscopy for Dysplasia and Cancer in Barrett's Esophagus", Digestic Diseases Week 2000 (American Gastroenterological Association, May 2000, San Diego, CA).

P.M. Ripley et al., "A Comparison of Artificial Intelligence Techniques for Spectral Classification in the Diagnosis of Human Pathologies based upon Optical Biopsy", Novel Biomedical Optical Spectroscopy, Imaging and Diagnostic (Optical Society of America, Apr. 2000, Miami, FL).

L. Lovat et al., "Novel 'Optical Biopsy' Technique using Elastic Scattering Spectroscopy for Dysplasia and Cancer in Barrett's Oesophagus", British Society of Gastroenterology Annual Meeting (Mar. 2000, Birmingham, UK).

Edinburgh, J. Bigio et al., "Developments in Endoscopic Technology for Oesophageal Cancer, Joint Symposium on Oesophageal Cancer", Abstract of Presentations from the Oesophageal Cancer Symposium organized jointly by the Royal College of Physicians of Edinburgh and the Royal; College of Surgeons of Edinburgh, Mar. 2000.

D.C. Pickard et al.,"Optical Biopsy: In–Vivo diagnosis of Breast Cancer using elastic Scatter Spectroscopy", Proceedings of SPIE, vol. 3907 BIOS 2000 (SPIE Biomedical optics symposium, San Jose, CA, Jan. 2000).

D.C. Pickard et al., "Elastic Scattering Spectroscopy In–Vivo: Optical Biopsies of Cancer of the Breast and GI Tract",vol. 3917 BOIS 2000 (biomedical optics symposium, San Jose, CA) SPIE Proceedings, Jan. 2000.

I.J. Bigio et al., "Diagnosis of Breast Cancer using Elastic–Scattering Sectroscopy: Preliminary Clinical Results", Journal of Biomedical Optics, vol. 5, No. 2, pp 221–228, (Apr. 2000).

Gavin M. Briggs et al., "Histological Assessment of Breast Tissue by Optical Biopsy", BASO Scientific Conference, British Association of Surgical Oncology, London (Nov. 2000).

Gavin M. Briggs et al., "Optical Biopsy for the Assessment of Sentinel Lymph Nodes of the Breast", BASO Scientific Conference, London (Nov. 2000).

M. Marenzana et al., "Optical Measurement of 3–D Collagen Gel Constructs by Elastic Scattering Spectroscopy", $2^{nd}$ Annual Symposium of the Tissue and Cell Engineering Society, Nottingham (Sep. 2000).

I Bigio and S.G. Brown, "Optical Biopsy for Minimally–Invasive Diagnosis of Breast Cancer", High Care 2000, $2^{nd}$ International Congress, Bochum, Germany (Feb. 2000).

Optical Biopsy for the Diagnosis of Breast Tumours, US Army Material Command, Atlanta, Georgia (Jun. 2000).

Irving J. Bigio et al., "Diagnosis of breast cancer using elastic–scattering spectroscopy: preliminary clinical results," *Journal of Biomedical Optics*, Apr. 2000, vol. 5, No. 2, pp. 221–228.

Judith R. Mourant et al., "Elastic Scattering Spetroscopy As a Diagnostic ool For Differentialting Pathologies In the Gastrointestinal Tract: Preliminary Testing," *Journal of Biomedical Optics*, Apr. 1996, vol. 2, pp. 192–199.

Miguel A. R.B. Castanho et al., "Separating the turbidity spectra of vesicles from the absorption spectra of membrane probes and other chromophores," *Eur Biophys J*, 1997, 26: pp. 253–259.

\* cited by examiner

SPECTRUM PROCESSING AND PROCESSOR

This invention was made with Government support under DAMD17-98-1-8343 awarded by the US Army Medical Research Acquisition Activity. The Government has certain rights in the invention.

CROSS-REFERENCE TO RELATED APPLICATIONS

This application claims priority under 35 U.S.C. §119 (b) to British Patent Application No. 0103030.3 filed Feb. 7, 2001, the disclosure of which is incorporated herein by reference in its entitety.

FIELD OF THE INVENTION

The invention relates to a method of processing a spectrum, in particular an elastic scattering spectrum taken from tissue and to apparatus including a spectrum processor for carrying out the method.

BACKGROUND ART

Elastic scattering spectroscopy is a known technique for investigating tissue. In essence, light is shone into human tissue, generally living human tissue, and a photoreceptor measures the light transmitted to the photoreceptor through scattering in the tissue. The spectrum of light passing through the tissue is then recorded, and used to assist in diagnosis of any of a number of medical conditions that the patient may have. Thus, the technique may be described as optical biopsy.

Prior art apparatus for carrying out optical biopsy is presented in WO98/27865 to David Benaron, and in U.S. Pat. No. 5,303,026 to Stroble et al. The latter patent describes a system having a light source feeding into a reference optical fiber and a probe optical fiber. The probe optical fiber being brought to a probe tip. The probe tip has another optical fiber arranged adjacently of it, which collects light and brings it to a detection system which compares its intensity to the intensity of light on the reference optical fiber. When the probe tip is brought against human tissue the detection system can record the difference as a between the reference signal strength and that of the light scattered by the human tissue as a function of wavelength to obtain an optical biopsy spectrum.

The use of an elastic scattering spectrum to diagnose a number of medical conditions is described in a number of papers. Zhengfang GE et al describe in the paper "Identification of Colonic Dysplasia and Neoplasia by Diffuse Reflectance Spectroscopy and Pattern Recognition techniques", Applied Spectroscopy Volume 52 number 6 (1998) p 833, a method of identifying colonic dysplasia and neoplasia. The paper describes a number of different pattern recognition techniques used to evaluate the samples.

One of these is multiple linear regression analysis, which is used to fit to reflectance intensities measured at 26 different wavelengths every 16 nm in the range 350 nm to 750 nm. An output score is obtained from the formula:

$$score = k + \sum_{j=1}^{26} a_j D_i(\lambda_j)$$

The coefficients $a_j$ are fitted coefficients arranged such that the score is +1 for adenomatous polyps and −1 for hyperplastic polyps. $D_i\lambda_j$ is the reflectance value for the ith tissue sample at the jth wavelength.

Another approach described in the paper by Zhengfang et al is linear discriminant analysis. This is a method of classifying a test into one of k groups using a classification score that can be computed from a formula. The test is classified into the group which gives the lowest classification score.

The classification of a test object $X_i=(x_1, x_2, \ldots x_d)$ containing d independent integers is assigned to one of k gropus using the classification score defined as $$D_k^2 = (X_i - \mu_k)^T M^{-1}(X_i - \mu_k)$$

where $M^{-1}$ is the inverse of the pooled covariance matrix over all classes $$M = \frac{1}{n} \sum_k \sum_{i=1}^{n_k} (X_i - \mu_k)(X_i - \mu_k)^T.$$

A third approach is backpropagating neural network analysis using a multilayer neural network with n input nodes, a hidden layer and an output layer. Neural network techniques have been widely reported and will not be discussed further here.

Other papers describe the use of elastic scattering spectroscopy in the diagnosis of a number of conditions. Backman et al describe the detection of precancerous epithelial cells in "Detection of Preinvasive Cancer Cells", Nature, vol 406 p35 (2000). Perelman et al, in "Observation of Periodic Fine Structure in Reflectance from Biological Tissue: A New Technique for Measuring Nuclear Size Distribution", Phys. Rev. Lett. vol 80 p627 (1998) describe periodic fine structure in mucosal membranes. The diagnosis of bladder cancer is described in "Spectroscopic Diagnosis of Bladder Cancer with Elastic Light Scattering" Mourant et al, Lasers in Surgery and Medicine, Volume 17 page 350 (1995). The use of elastic scattering to diagnose pathologies in the gastrointestinal tract is described in "Elastic Scattering Spectroscopy as a diagnostic tool for differentiating pathologies in the Gastrointestinal tract: preliminary testing", Mourant et al, Journal of Biomedical optics, Vol 1 p192, and in "Ultraviolet and visible spectroscopies for tissue diagnostics: fluorescence spectroscopy and elastic scattering spectroscopy", Bigio and Mourant Phys. Med. Biol. Volume 42 p803 (1997).

It is thus clear that the use of elastic scattering spectroscopy is attracting interest as a diagnostic tool. In spite of this research interest the most reliable approach presently used for detection of cancer in tissue and other conditions is histology. However, this is time consuming and laborious and in many situations, especially for diagnosing cancer, multiple biopsies may be needed.

There is thus a need to develop optical techniques further. One application is to guide conventional biopsies, avoiding false negatives and reducing the number taken while increasing yield. The long-term goal is to develop the techniques to a point where they can be used rapidly, efficiently and reliably to diagnose conditions without the need for histology.

SUMMARY OF THE INVENTION

According to the invention there is provided a method of processing a broadband elastic scattering spectrum obtained from tissue comprising the steps of: obtaining, in a plurality of fitting ranges of wavelength, fitting parameters giving the best fit to the spectrum in the respective fitting ranges; and recording the fitting parameters as a parameter data set representing the spectrum; wherein in at least one fitting range the fit is to the absorption of at least one predetermined component, and in the remainder of the fitting ranges the fit is to a smooth function.

By fitting in a number of different fitting regions to known absorption spectra and to a smooth function a measured spectrum including a large number of data points can be reduced to the very much smaller number of data points, i.e. the fitting parameters. Subsequent data processing using the fitting parameters instead of the whole spectrum (as used in the prior art discussed above) may allow simpler, more reliable and more rapid assessment of the patient's condition.

The method can be thought of as using model dependent fitting, i.e. of analysing the spectrum using a model of the absorption with certain absorbing components absorbing at certain frequencies before carrying out any diagnosis or discrimination.

The fit to the absorption of at least one predetermined component may be to the absorption line shape of the at least one predetermined absorbing component. In particular, the fit may use a parabolic approximation to the peak of absorption of that absorbing component.

The fit to the absorption of at least one predetermined component may be a fit to an absorption spectrum previously measured using an optical biopsy probe on a sample of the predetermined absorbing component in a tissue-like matrix. This absorption spectrum, in general, differs from the simple absorption spectrum due to scattering obtained from a conventional optical transmission cell and available in most textbooks. The use of a spectrum measured using an optical biopsy probe on a sample in a tissue-like substrate has not previously been suggested, as far as the inventor is aware.

Alternatively, especially for single component systems, the fit may be nothing more than determining the excess of absorption in the spectrum at a predetermined frequency over the background spectral lineshape due to scattering calculated by extrapolating a straight line fit in a neighbouring region of the spectrum. The predetermined frequency is preferably the peak absorption wavelength of the absorbing component.

The fit to a smooth function is preferably to a straight line. Such fits are straightforward to carry out and with suitable choice of fitting ranges can parameterise an absorption slowly varying with wavelength, i.e. the spectral lineshape due to scattering in the absence of any absorption features.

The fitting ranges, taken together, preferably include at least 60%, further preferably 80% of the wavelength range of the complete broadband elastic spectrum, at least in the range in which the spectrum has been measured with reasonable accuracy. In this way substantially all of the measured spectrum may be parameterised.

The method may also include, after obtaining fitting parameters in one fitting range, calculating a modified spectrum to compensate for the shape of the spectrum represented by the fitting parameters in that fitting range, and using the modified spectrum when fitting parameters in at least one further fitting range. This may be done by inputting the recorded fitting parameters in that fitting frequency range into a model of the absorption, calculating the expected absorption spectrum determined by the model with the input fitting parameters and subtracting the calculated absorption spectrum from the initial spectrum to obtain the modified spectrum used when fitting parameters in at least one further fitting range.

It should be noted that the fitting regions may overlap. For example, it may be desired to fit to a line shape of a known absorption component in a certain fitting region and then to multiply by a predetermined function to remove that line shape. However, there may still be information in the residual intensity of the lineshape due to scattering and this can be fitted using linear fitting parameters in a fitting region that may overlap or even be identical to the fitting region used to fit to the line shape of the absorption component.

The preprocessed spectrum may be fed to a discriminating algorithm to determine whether or not the data corresponds to one or more medical conditions. The discriminating algorithm may be trained to detect a particular medical condition or to discriminate between a number of clinically similar conditions. The training will use a number of training samples. The skilled person will realise that there are a number of suitable models with a number of variable fitting parameters for implementing the discriminating algorithm. For example, a neural network approach may be used, a linear discriminant analysis or a hierarchical cluster analysis. All of these are known per se, and the first two are, for example, discussed in the paper by Zhenzhou et al mentioned above. It is generally the case, however, that the smaller number of model dependent fitting parameters obtained using the preprocessing method according to the invention can provide a benefit whatever fitting and diagnosis approach is used.

One reason for the improvement is the reduction in the number of points in the data set for fitting. Whether using a neural network or other discriminant analysis, the large number of points in the original data set of the whole spectrum means that a large number of training samples would be needed to train any model of the results output from the preprocessor. By reducing the number of points in the data set to be fitted less training is required and the fit can be carried out more reliably.

A preferred approach is hierarchical cluster analysis in which the n parameters of the spectrum define a unique point in n-dimensional space. Clusters of points are determined—the diagnosis corresponds to identifying in which cluster a measured spectrum point lies. Hierarchical cluster analysis has the advantage that it allows a "don't know" response, if for example the measured point is located far from any of the clusters identified. This is of advantage in preventing false diagnosis in cases where no such diagnosis can be reliably made.

A number of different absorbing components can be fitted and each absorbing component will absorb in a different wavelength range and hence a different fitting range.

One example of general application in human tissue is to fit to the haemoglobin absorption; this can be done by fitting to the saturation and the total hematocrit concentration. The saturation is defined as the percentage of oxygenated haemoglobin to the total hematocrit (oxygenated and deoxygenated haemoglobin). Such a fit to haemoglobin concentration may be carried out in a fitting range including at least part of the region of the spectrum from 320 nm to 620 nm.

Haemoglobin gives rise to an absorption feature which may dominate the spectrum in the region of 415 nm, called the Soret band. Other constituents of tissue also absorb near this wavelength and once the "normal" Hb absorption has been removed the absorption due to these features will be observed and may be fitted. The other features may be the absorption due to components such as cytokines.

Other absorbing components are relevant to a number of different kinds of spectrum. For example, to detect breast cancer it is preferred to fit to the beta-carotene absorption spectrum in the fitting range 400–520 nm.

In some studies, exogenous dye may be introduced into tissue for diagnostic purposes and accordingly the preprocessing method can include fitting to the spectrum of the dye used. For example for, for suspected cases of breast cancer, blue dye can be introduced into human tissue to trace the spread of the disease. For the dye used in studies to date, Patent V blue dye (Trade Mark), a fitting range including at least past of the range 530 nm to 720 nm is suitable.

One predetermined fitting region may be a region in the range 630 nm to 810 nm, and the fit may be a linear fit in this region. The method may also include fitting to a linear model in a number of other regions. These can include linear fitting in the range 340 nm to 360 nm, and/or the range 320 nm to 330 nm. These fittable regions will be observed after the removal of absorption features.

The spectral trace may be checked for and the spectrum rejected if the check reveals measurement errors or unsuitable data. For example, it may be advisable to check for a minimal transmitted intensity in the Soret band and to reject the spectrum if the measured transmitted intensity is substantially zero in this band. In other words, if the measured transmitted intensity is less than 10% full scale, preferably less than 5% full scale, the spectrum may be rejected. Another possibility is to check for interference from background illumination and to reject the spectrum if background illumination is too high. Further, the spectrum can be checked for contact between probe and tissue.

The invention also relates to a method including recording an elastic scattering spectrum from tissue, and preprocessing the spectrum as described above.

The tissue may be in vivo, i.e. tissue incorporated in the living human body.

The tissue may be in vitro, i.e. tissue removed from the body.

In another aspect there is provided a method comprising the steps of recording an elastic scattering spectrum; preprocessing the spectrum using a preprocessing method to obtain a plurality of fitting parameters characterising the spectrum; testing the preprocessed spectrum using a discriminant model; and outputting a result based on the model.

The result may be an output indicating to which class, if any, the recorded elastic scattering spectrum belongs. The output may thus be a diagnosis.

In embodiments, the discriminant model may be a neural network, linear discrimination, hierarchical cluster analysis or other methods as are known to those skilled in the art.

The preferred discriminant model uses hierarchical cluster analysis. This groups data into unbounded class regions permitting "not sure" diagnostic indications, rather than forcing a decision and risking a false diagnosis.

In another aspect, the invention relates to a method comprising the steps of recording an elastic scattering spectrum from tissue; processing the spectrum to produce a number of parameters characterising the spectrum; determining to which, if any, of a number of classes the parameterised spectrum belongs; and outputting the class, if any, to which the spectrum is determined to belong.

In a further aspect there is provided a training method comprising the steps of recording a plurality of optical biopsy spectra from tissue for which it is known whether the tissue displays a predetermined medical condition; preprocessing each of the spectra using a method as defined above; and training a discriminant model using the preprocessed spectra.

In another aspect there is provided an apparatus for optical biopsy, comprising apparatus for elastic scattering spectroscopy of tissue, including a light source for emitting light over a broad range of frequencies; a probe for transmitting light from the light source to tissue and for receiving light scattered in the tissue; a spectrometer for measuring the intensities of the received light as a function of frequency; and a processor for processing the measured light spectrum arranged to carry out the method as described above.

The apparatus may include a first optical fiber bringing light from the light source to a probe tip; and a second optical fiber bringing scattered light from the probe tip to the spectrometer; wherein the ends of the first and second fibers at the probe tip are arranged adjacently spaced apart by a predetermined distance.

The apparatus may include a decision processor for checking the fitted parameters against the results for one or more predetermined medical conditions and outputting the best fit medical condition based on the decision processor output.

BRIEF DESCRIPTION OF THE DRAWINGS

Specific embodiments of the invention will now be described, purely by way of example, with reference to the accompanying drawings in which.

DETAILED DESCRIPTION

Figure 1:
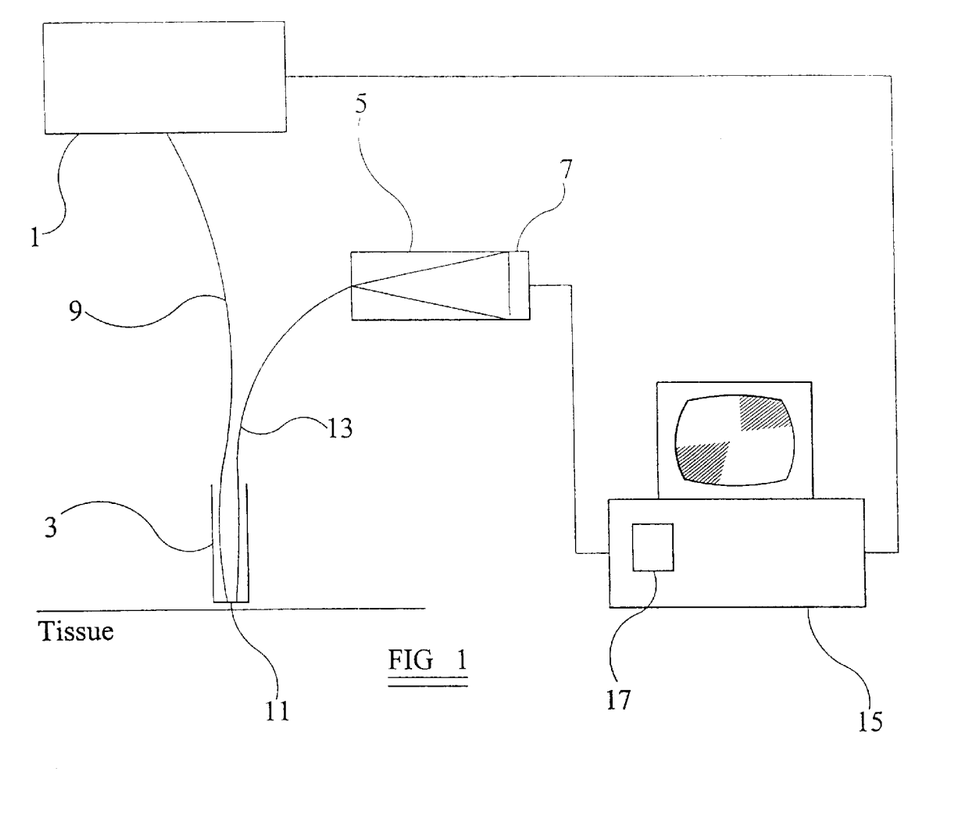
FIG. 1 shows an optical biopsy system.

The first step is to record an elastic scattering spectrum. Referring to FIG. 1, the apparatus for recording the spectrum includes an excitation light source 1 and a probe 3. A spectrometer 5 for splitting light and a detector array 7 for measuring the intensity of the split light are also provided. A first optical fibre 9 transmits light from the light source 1 to the end 11 of the probe and a second optical fibre 13 picks up light from the end of the probe and transmits it to the spectrometer for measurement. A computer 15 including interface electronics is electrically connected to the light source 1 the spectrometer 5 and the detector 7 for controlling these parts. The apparatus may be as described in U.S. Pat No. 5,305,026 (discussed above) but this is not required and the skilled person will readily conceive of alternative probes, light sources and spectrometer arrangements.

In use, the end 11 of the probe is brought up to a tissue sample, such as the skin of a patient, so that the ends of the first and second optical fibre are adjacent to tissue. Light is then emitted from the excitation light source, passes through the first optical fiber 9 and into the tissue. After passing through and being scattered in the tissue some of the scattered light enters the second optical fiber 13 and passes to the spectrometer where the spectrum is measured.

In the specific example the excitation light source 1 is a xenon arc light which emits a number of pulses down the send fiber. The output detected at the spectrometer 5 is integrated to catch the response from the plurality of pulses. The spectrum is "auto-ranged" to ensure that the peak intensity at a chosen wavelength is scaled to lie above some threshold wavelength but below the saturation level of the detector 7, in this instance a CCD, by varying the number of light pulses. A second spectrum without illumination is obtained immediately before or after the illuminated spectrum is taken and the second spectrum is subtracted from the illuminated spectrum. This removes effects due to extraneous light sources such as room lights, operating theatre lights or the headlamps of an endoscope.

The measured spectrum is then ratioed to a reference spectrum which is that obtained from a white material with constant reflection properties from the UV to the IR. Such a material is commercially available under the trade name "Spectralon". The resultant spectrum is then a ratio to a nominal mean intensity level 100. This removes any effects due to the spectrum of the light source. Next, the spectrum is smoothed using a simple "boxcar" function with a unit length of 7 pixels.

Figure 4:
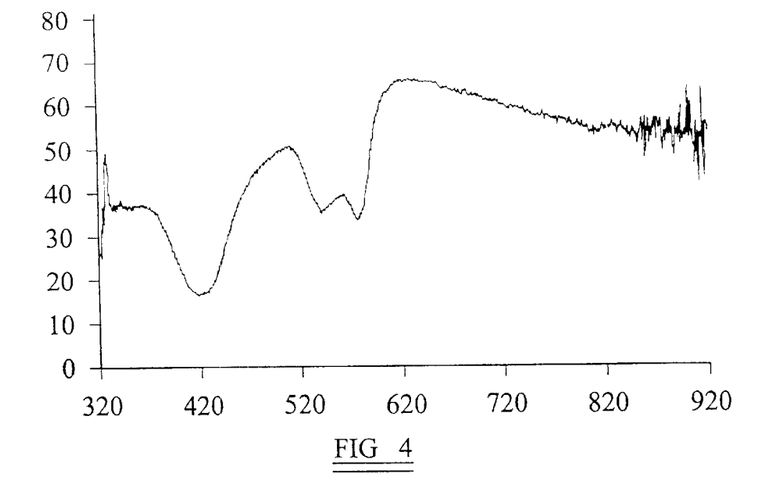
FIG. 4 is a first example spectrum, taken from normal tissue.
Figure 5:
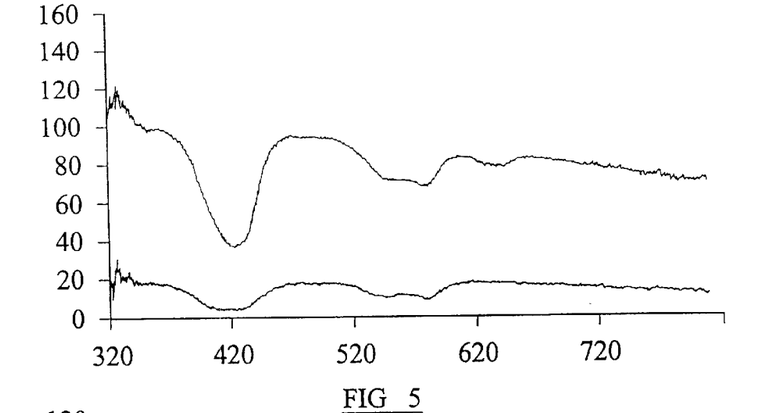
FIG. 5 is an example spectrum showing interference from background illumination.

An example of the spectrum thus achieved is shown in FIG. 4. This is the spectrum that forms the starting point for preprocessing. The processing of the spectrum is carried out by a program 17 stored in the computer 15 for causing the computer to carry out the steps of the method that will now be described which will now be described with reference to FIG. 2.

Figure 2:
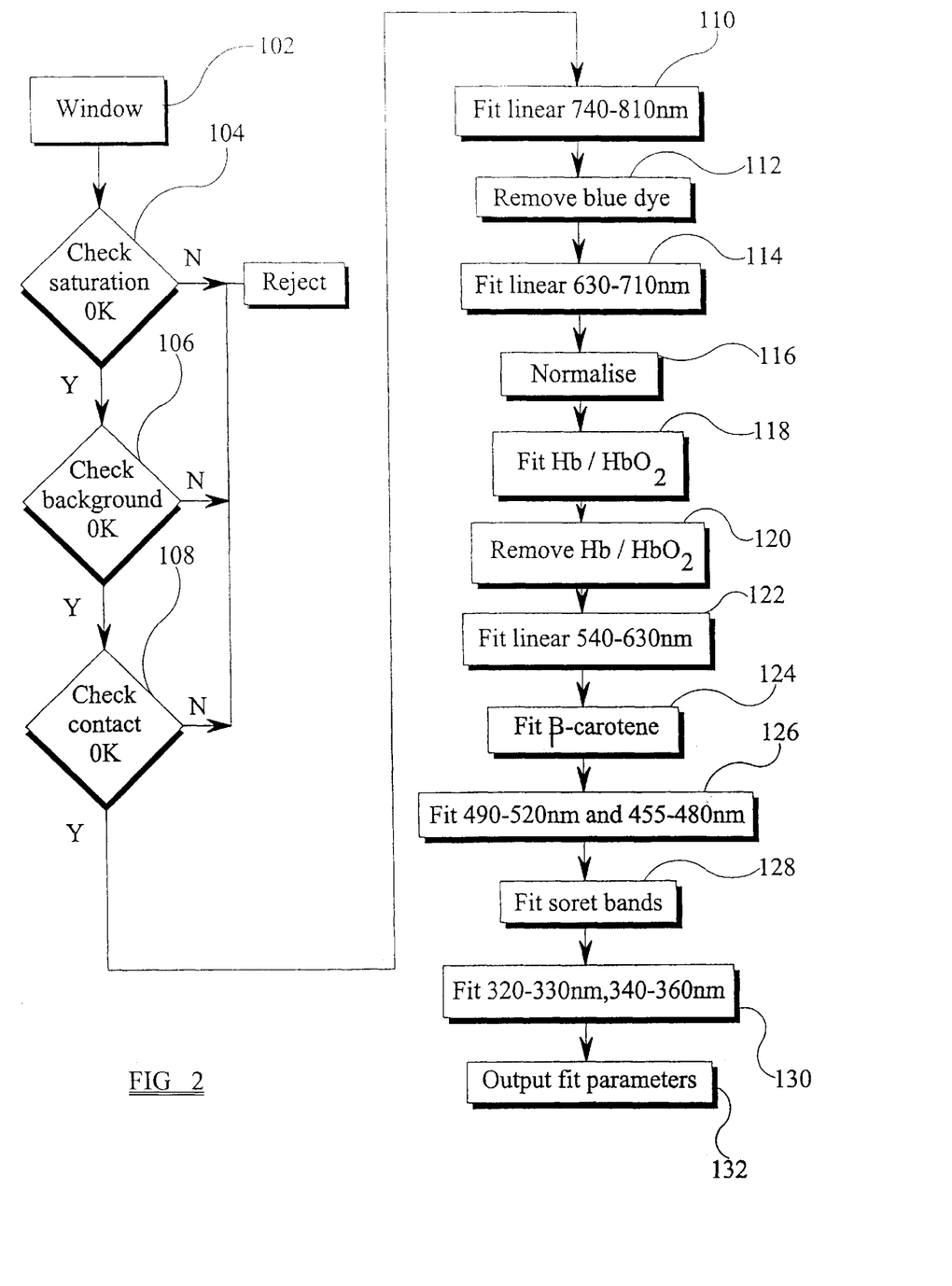
FIG. 2 is a flow diagram of a preprocessing method according to a first embodiment of the invention.

The first step 102 is to define the useable wavelength range. This is principally determined by the noise in the spectrum and generally lies in the range 320–810 nm. Results outside this predetermined window are rejected. The skilled person will realise that when using different light sources to the Xenon light or different probe components useable results may be achieved over a different wavelength range and in that case a different wavelength window can be used.

The spectrum is then checked (Step 104) for measurement errors. In particular, it is common for the absorption peaks of oxygenated haemoglobin $HbO_2$ and deoxygenated haemoglobin Hb at 415 nm and 433nm to be saturated if too much blood is present in the tissue sample. That is to say, the measured light intensity may be substantially zero in this region. If this is the case the absorption is judged to be too great and the spectrum rejected.

The next check, in step 106, is to determine if the signal has been corrupted by background illumination. This can occur in one of two ways. If the illumination is too bright the CCD may become saturated. This can easily be checked for by determining if the peak signal level is too low; if it is the spectrum is rejected.

Another possibility is that sample movement between the tissue sample and the probe has occurred between the taking the illuminated and the dark measurements. This is a particular problem for endoscopic measurements made in the gut since gut tissue is highly active. This effect has been observed to give rise to a peak or trough between 600 and 655 nm. The existence of such a peak of trough is detected and if present the sample is rejected. Alternatively the recorded spectrum may be modified to eliminate this artefact.

Figure 6:
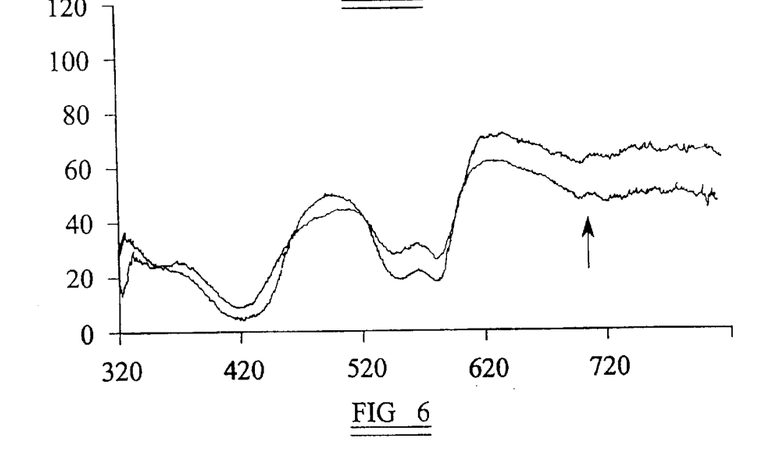
FIG. 6 is an example spectrum showing a small peak around 690 nm.

A third check is then carried out in step 108 for good contact between probe and tissue. Imperfect contact appears to give a V-shaped feature at 690 nm, as illustrated in both spectra shown in FIG. 6, which can be checked for. Again, if the feature is present the spectrum can be rejected.

Assuming that the spectrum is acceptable after the above checks the next step in this example is to fit linear regions. It appears that the spectrum is approximately linear between 630 nm and 810 nm but better results are obtained by fitting in two regions, from 740 to 810 nm (step 110) and from 630 to 710 nm (step 114). There are a number of reasons for this. As mentioned below, blue dye can disturb the region below 730 nm. Secondly, the haemoglobin tail can extend to well above 630 nm. Thirdly, absorption due to water gives rise to a small non-linearity around 730 nm.

The fitting is carried out using conventional linear regression to fit a region of the spectrum to a straight line gradient m and intercept b. As is known, m and b are given by:

$$m = \frac{n\sum_{i}^{n} x_i y_i - \sum_{i}^{n} x_i \sum_{i}^{n} y_i}{n\sum_{i}^{n} x_i^2 - \left(\sum_{i}^{n} x_i\right)^2}$$

$$b = \frac{\sum_{i}^{n} y_i \sum_{i}^{n} x_i^2 - \sum_{i}^{n} x_i \sum_{i}^{n} x_i y_i}{n\sum_{i}^{n} x_i^2 - \left(\sum_{i}^{n} x_i\right)^2}$$

where the subscripts i represent summation over the points in the fitted region.

Between fitting these two steps any absorption caused by blue dye may be removed in step 112. When used for the identification of sentinel nodes in breast tissue a blue dye, known as Patente Bleu V (Trade Mark) is used which has an absorption band with a peak at 635 nm. The blue dye spectrum is removed in the same way as used for fitting to haemoglobin features, as explained below.

Figure 7:
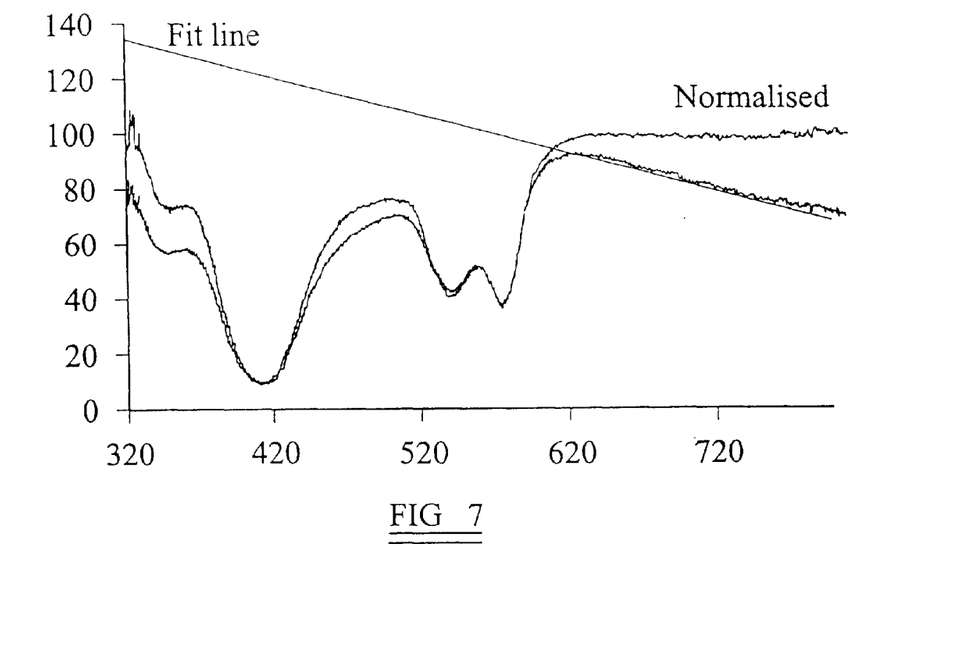
FIG. 7 illustrates normalisation.

After fitting to the 630 nm to 710 nm region the spectrum is normalised (step 116) to the gradient in the 630–710 nm linear section. In other words, the ratio to a line of constant gradient is taken for the whole spectrum so that the region of the spectrum between 630 and 710 nm becomes flat. This is illustrated in FIG. 7 which shows the original spectrum, a line of constant gradient fitted in the region between 630 nm and 710 nm and the normalised spectrum normalised so that the graph is flat in the region 630 nm to 710 nm.

Next, in step 118, haemoglobin lines are fitted and compensated.

In general, optical absorption is given by the well-known Beer-Lambert law, which states that the intensity of light remaining in a beam that has passed through a thickness z of material which has an absorption coefficient of γ is given by $I=I_o e^{-\gamma z}$, where $I_o$ is the incident intensity. Conventional absorption spectra can readily be obtained in the published literature.

However, in tissue, the situation is more complicated and scattering effects must be taken into account. In elastic scattering spectroscopy, the situation is more complex still and the path-length through which photons travel through tissue is not well defined. Indeed, the path length varies non-linearly with the wavelength of light. Accordingly, published spectra of components may not be suitable and the absorption spectra used in the present invention are spectra measured using the equipment described above and in-vitro tissue phantoms. The spectra used thus implicitly compensate for the geometry and so the accuracy of absorption measurement and removal is enhanced.

For simple, one-component absorption, the amount of a component may be estimated using an offset from a straight line fit to an adjacent region. In the embodiment described, this is done by normalising the graph in the adjacent region and then calculating the offset from this absorption at the known frequency peak. This process is used for blue dye and beta carotene in the described embodiment, but as the skilled person will realise the process can also be used for other one-component systems.

For haemoglobin there is more than one absorber (Hb and $HbO_2$) and the amount of haemoglobin must be measured using some form of fit. This is done by fitting the peak regions to a parabolic line shape and using a regression analysis in a known way.

Figure 8:
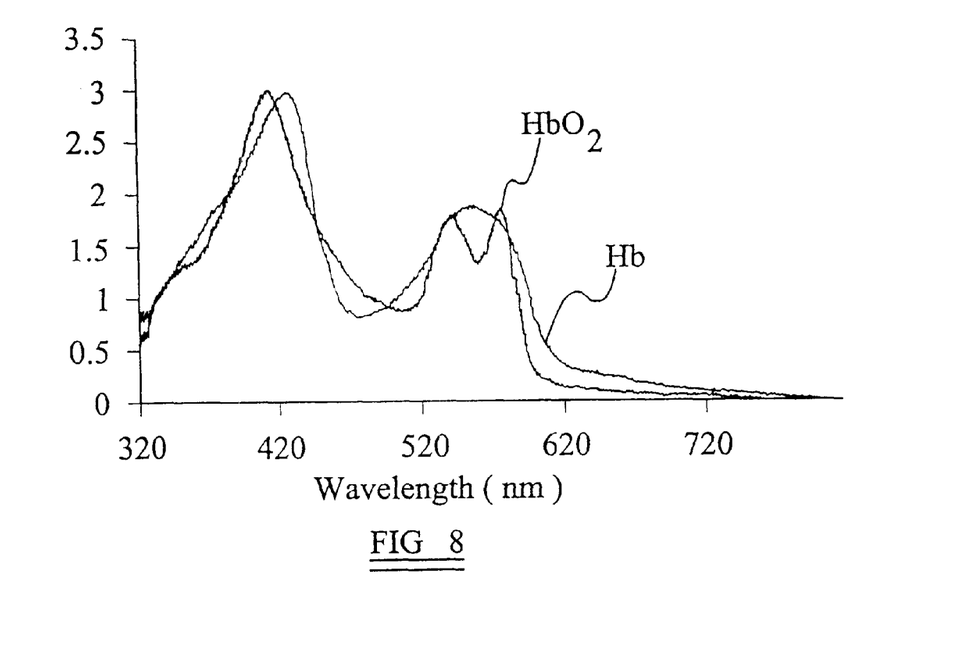
FIG. 8 shows haemoglobin absorption.

Accordingly, the peaks in the absorption spectrum at which the measurements should be taken are defined. Referring to FIG. 8, which shows absorption spectra for oxygenated ($HbO_2$) and deoxygenated haemoglobin (Hb), differences in the absorption profiles are obvious. After the normalisation of step 116, the wavelength positions and absorption coefficients in the vicinity of peaks in this spectrum are fitted to using a local parabolic approximation and multiple linear regression analysis.

It may be useful to find points of equal absorption for both components and the absorption values for the second spectrum at positions corresponding to peaks in the first.

Once these values have been found as fit parameters these are converted into absorption coefficients. The fitting values be used to calculate the saturation, defined as the percentage of oxygenated haemoglobin to total haemoglobin concentration, known as hematocrit.

Figure 9:
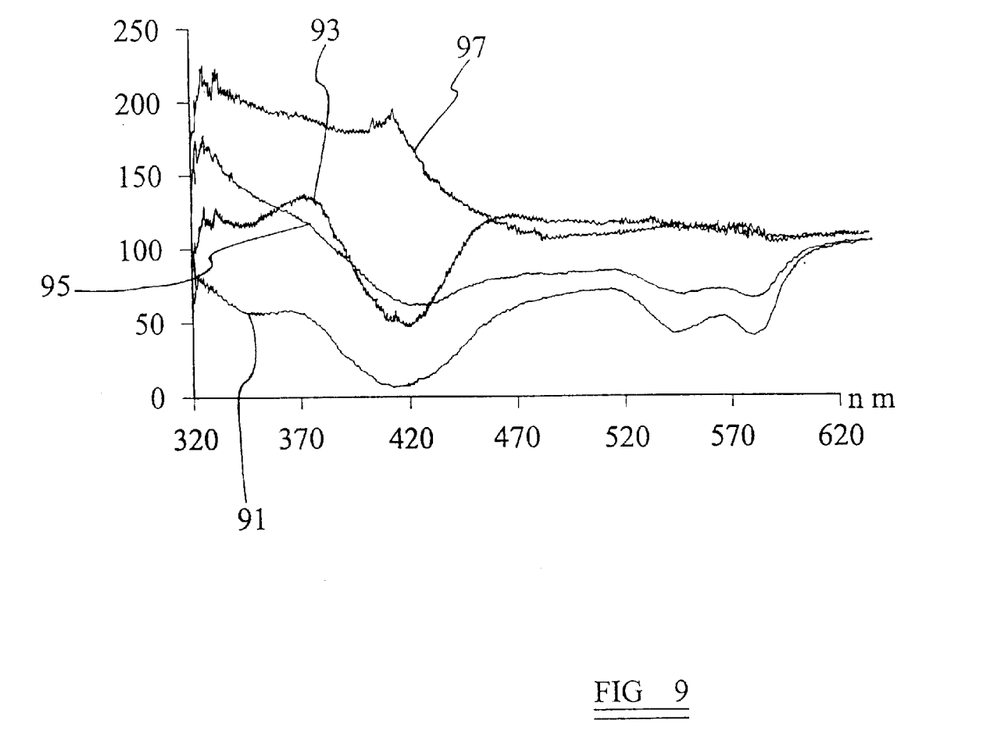
FIG. 9 shows the spectrum after haemoglobin absorption has been compensated.

The fitting parameters are then used to compensate the absorption represented by these fitting parameters and subtract that from the spectrum. The absorption calculated in the model from the fitted concentrations of haemoglobin is determined and subtracted (step 120) from the measured spectrum to obtain the spectrum used in subsequent steps. Two pairs of spectra before and after this subtraction are shown in FIG. 9. Spectrum 91 (before) becomes spectrum 93 (after), and spectrum 95 (before) becomes spectrum 97 (after) illustrated in FIG. 9.

The process of removal used in the embodiment relies on the assumption that the Beer-Lambert function describes the absorption sufficiently well and that the in-vitro absorption spectrum does not differ substantially to the in-vivo spectrum. The removal process is straightforward. The model used is simply to reverse the model used in the initial absorption process. Each point in the model spectrum is simply multiplied by a factor obtained from the fitted concentration by inverting Beer-Lambert's law to determine a model spectrum that can then be subtracted from the measured spectrum.

Although haemoglobin shows marked non-linearities in absorption at high concentrations this should not present a problem in samples that pass the test of step 104 above and have sufficiently little haemoglobin.

Although the subtraction does not, in general, completely eliminate the haemoglobin peaks, and indeed the effect is sometimes to invert the peaks, what the step does do is to remove from the spectrum those features already recorded by the haemoglobin fitting parameters.

The skilled person will realise that there are a number of alternative ways to calculate the haemoglobin concentrations from the measured data. Rather than just fitting to the peaks, an alternative is to calculate the saturation from the isobectic point (the point at which both components are absorbed equally. The absolute absorption might then be used to calculate the total hematocrit.

In step 122, a linear fit is made in the region 540 to 630 nm.

In step 124, the absorption due to beta-carotene is fitted, recorded and then the absorption spectrum of beta-carotene subtracted from the measured spectrum. This fit takes place in a fitting range beginning at around 520 nm and extending down to include at least distinct peaks at 480 nm, 450 nm and 420 nm. Accordingly, the fitting range used may be all or part of the range 400 nm to 520 nm. Fitting to a Beta-carotene peak and consequently obtaining fitting parameters related to the concentration of Beta carotene is particularly important in pre-processing data from breast tissue, since beta carotene is related to vitamin C and found only in fat. Its presence is a contra-indication to malignancy.

Linear regions between 490 nm and 520 nm and between 455 nm and 480 nm are fitted. (step 126). As before, the gradients, intercept intensities and regression statistics are recorded.

Then in step 128, the residual absorption to other chromophoric components within the region of the Hb Soret band at around 415 nm is measured by parabolic approximation. This gives an indication of the different profile of cytokines and other tissue absorbers in the tissue as apposed to normal, whole blood.

Next, linear fits are provided in the regions of 340 to 360 nm and also 320 to 330 nm.

Although it may appear that a large number of fits have been carried out, the number of data points required to parameterise all of the fits is very much less than the number originally measured, which in the apparatus used is of order 1800 data points. The reduced number of data points can readily be used as the inputs to subsequent models, for example to train a model or to diagnose based on a previously trained model.

In order to use the data measured for diagnosis, it is first necessary to "train" a model by providing it with a number of fitted spectra for which it is known whether the tissue is normal or has a given medical condition in order to then be able to then use the test to determine whether another patient has that condition without the need for histology.

In the preferred embodiment, hierarchical cluster analysis is used. In hierarchical cluster analysis points in an n-dimensional space are grouped into a hierarchy of clusters. The grouping may occur from the bottom up, in which case each point is assigned to a single point cluster, and an algorithm groups pairs of clusters one after the other to produce a family tree of clusters. Alternatively, it is also known to successively divide clusters to produce a hierarchy from the top down.

Hierarchical cluster analysis is known, for example for face recognition and other pattern recognition. Its use in diagnosis from elastic scattering spectra is mentioned in Paul M Ripley, D. Pickard et al. "A Comparison of Artificial Intelligence Techniques for Spectral Classification in the Diagnosis of Human Pathologies based upon Optical Biopsy" Novel Biomedical Optical Spectroscopy, Imaging and Diagnostics (Optical Society of America, Apr. 200, Miami, Fla.) OSA Biomedical Topical Meetings Proceedings, 2000, MC5.

Figure 3:
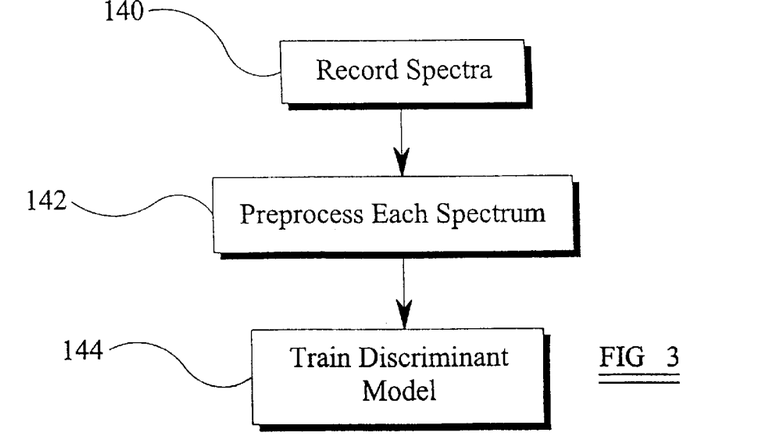
FIG. 3 is a flow diagram of an optical biopsy method using the preprocessing of FIG. 2.

To train the model, a number of test samples of known diagnosis are taken (step 140); the samples are known as the training set. The training samples are then preprocessed as described above (step 142), and divided into clusters using hierarchical cluster analysis (step 144). Hierarchical cluster analysis is described, for example, in Duda, Hart and Stork "Pattern classification: $2^{nd}$ edition", John Wiley & Sons, California, USA, 1998, and Andre Hardy "On the number of clusters", Computational Statistics & Data Analysis, volume 23 pages 83–96, 1996.

Each of the clusters is assigned a rating based on the points in the cluster. For example, if most of the points in the cluster based on the training set have the given medical condition, the cluster is labelled "suspicious". Conversely, if the majority of points in the cluster are clear of that condition, the cluster is labelled "clear".

Then, when an elastic scattering spectrum of a patient is taken, the point represented by the fitting parameters is determined and its Euclidean distance to each cluster is determined in the multidimensional parameter space spanned by the fitting parameters. If the point is further than a predetermined distance from any cluster, then a "don't know" result is given. Otherwise, the point is close to a cluster and it is assigned to the closest cluster and the label corresponding to that cluster is output as a diagnosis. This technique is known as the "leave one out" approach in hierarchical cluster analysis.

The method of the invention is particularly useful in diagnosing a number of conditions, for example breast cancer, dysplasia within the gastro-intestinal tract, cancers of the oral mucous, cervical cancer, lung cancer and skin cancer.

Although the invention has been described with reference to a specific example, the skilled person will realise that a number of variations are possible. In particular, a number of other predetermined components may be fitted for.

For example, a fit to the absorption line shape of bile pigment may be carried out in a fitting range including at least part of the range from 230 nm to 512 nm.

A fit to melanin absorption may be carried out using a large fraction of the whole spectrum as the fitting range; the fit may be carried out after fits to other absorbing components have been carried out and the absorption due to the other components subtracted from the measured spectrum.

A fit to protein absorption may be carried out below 350 nm.

Furthermore, although the invention as described above uses the wavelength as the abscissa of the spectrum, it is possible instead to use frequency or any other parameter related to wavelength as the abscissa.

What is claimed is:

1. A method of processing a broadband elastic scattering spectrum obtained from tissue comprising the steps of:
    obtaining, in a plurality of fitting ranges of wavelength, fitting parameters giving a best fit to the spectrum in the respective fitting ranges; and
    recording the fitting parameters as a parameter data set representing the spectrum; wherein
        in at least one fitting range, but not all fitting ranges, the best fit is to an absorption of at least one predetermined component; and
        in the remainder of the fitting ranges, the best fit is to a smooth function.

2. A method according to claim 1 wherein the fit to the smooth function is to a straight line.

3. A method according to claim 1 wherein the plurality of fitting ranges, taken together, include at least 60% of the wavelength range of the complete broadband elastic scattering spectrum.

4. A method according to claim 1 wherein in at least one fitting range, the fit to the absorption of at least one predetermined component is to the absorption line shape of the at least one predetermined component.

5. A method according to claim 4 wherein the fit to the absorption line shape of the at least one predetermined component uses a parabolic approximation.

6. A method according to claim 1 wherein the fit to the absorption of at least one predetermined component is a fit to an absorption spectrum previously measured using an optical biopsy probe on a sample of the predetermined component in a tissue-like matrix.

7. A method according to claim 1 further comprising, after the step of obtaining fitting parameters in one fitting range, calculating a modified spectrum to compensate for the shape of the spectrum represented by the fitting parameters in that fitting range, and using the modified spectrum when fitting parameters in at least one further fitting range.

8. A method according to claim 7 wherein after obtaining fitting parameters representing a fit to an absorption line shape in one fitting range, a modified spectrum is calculated by inputting the recorded fitting parameters in that fitting wavelength range into a model of the line shape absorption, calculating an expected absorption spectrum determined by the model with the input fitting parameters and subtracting the calculated absorption spectrum from the initial spectrum to obtain the modified spectrum used when fitting parameters in at least one further fitting range.

9. A method according to claim 1 wherein, in at least one fitting range, the predetermined components are haemoglobin in oxygenated and deoxygenated forms.

10. A method according to claim 9 wherein the fitting range in which the predetermined absorption components are oxygenated and deoxygenated haemoglobin is at least part of the range from 320 nm to 620 nm.

11. A method according to claim 1 wherein in one fitting range in the range 400 to 520 nm the predetermined component is beta-carotene.

12. A method according to claim 1 including calculating absorption of other chromophoric components in the tissue which share haemoglobins Soret absorption band in the range of approximately 412 nm to 430 nm and recording differential absorptions as fitting parameters.

13. A method according to claim 12 wherein the chromophoric components include cytokines.

14. A method according to claim 1 wherein in a fitting range including at least part of the range from 230 nm to 512 nm the predetermined component is a bile pigment.

15. A method according to claim 1 wherein in a fitting range covering substantially the whole of the spectrum the predetermined component is melanin.

16. A method according to claim 1 including fitting in a range below 350 nm to protein absorption.

17. A method according to claim 1 wherein in a fitting range the predetermined component is an exogenous dye.

18. A method including recording an elastic scattering spectrum from tissue, and preprocessing the spectrum using a method in accordance with claim 1.

19. A computer program product for processing a broadband elastic scattering spectrum obtained from tissue, the computer program product for loading into a computer arranged to cause the computer to carry out the steps of:
    obtaining, in a plurality of fitting ranges of wavelength, fitting parameters giving a best fit to the spectrum in the respective fitting ranges; and
    recording the fitting parameters as a parameter data set representing the spectrum; wherein
        in at least one fitting range, but not all fitting ranges, the best fit is to an absorption of at least one predetermined component; and
        in the remainder of the fitting ranges, the best fit is to a smooth function.

20. Apparatus for analysing an elastic scattering spectrum taken from tissue, comprising:

a data store for recording the elastic scattering spectrum;

a processor arranged to obtain a plurality of fitted parameters characterising the spectrum by carrying out the steps of:
- obtaining, in a plurality of fitting ranges of wavelength, fitting parameters giving a best fit to the spectrum in the respective fitting ranges; and
- recording the fitting parameters as a parameter data set representing the spectrum; wherein
  - in at least one fitting range, but not all fitting ranges, the best fit is to an absorption of at least one predetermined component; and
  - in the remainder of the fitting ranges, the best fit is to a smooth function.

21. Apparatus for elastic scattering spectroscopy of tissue, including
- a light source for emitting light in a broad frequency band;
- a probe for transmitting light from the light source to tissue and for receiving light scattered in the tissue;
- a spectrometer for measuring the spectrum of the received light as a function of frequency; and
- a processor for processing the measured light spectrum arranged to obtain a plurality of fitted parameters characterising the spectrum by carrying out the steps of:
  - obtaining, in a plurality of fitting ranges of wavelength, fitting parameters giving a best fit to the spectrum in the respective fitting ranges; and
  - recording the fitting parameters as a parameter data set representing the spectrum; wherein
    - in at least one fitting range, but not all fitting ranges, the fit is to ths absorption of at least one predetermined component; and
    - in the remainder of the fitting ranges, the fit is to a smooth function.

22. Apparatus according to claim 21 wherein the probe contains a first optical fiber bringing light from the light source to a probe tip; and
- a second optical fiber bringing scattered light from the probe tip to the spectrometer; wherein the ends of the first and second fibers at the probe tip are arranged adjacently spaced apart by a predetermined distance.

23. Apparatus according to claim 21 further comprising a decision processor for checking the fitted parameters against results for one or more predetermined medical conditions and outputting a best fit medical condition based on the decision processor output.

24. Apparatus according to claim 23 wherein the decision processor uses hierarchical cluster analysis.

25. A training method comprising the steps of:
- recording a plurality of broadband elastic scattering spectra from patients for which it is known whether they have a predetermined medical condition;
- obtaining, in a plurality of fitting ranges of wavelength, fitting parameters giving a best fit to the spectrum in the respective fitting ranges; and
- recording the fitting parameters as a parameter data set representing the spectrum;
- the first recording step, the obtaining step, and the second recording step resulting in a preprocessed spectra; wherein
  - in at least one fitting range, but not all fitting ranges, the best fit is to an absorption of at least one predetermined component;
  - in the remainder of the fitting ranges, the best fit is to a smooth function; and
- training a discriminant model using the preprocessed spectra.

* * * * *